United States Patent [19]
Hunicke-Smith

[11] Patent Number: 6,132,996
[45] Date of Patent: Oct. 17, 2000

[54] THERMOCYCLING APPARATUS AND METHOD

[75] Inventor: Scott P. Hunicke-Smith, Menlo Park, Calif.

[73] Assignee: The Board of Trustees of the Leland Stanford Junior University, Stanford, Calif.

[21] Appl. No.: 09/246,539

[22] Filed: Feb. 8, 1999

Related U.S. Application Data

[62] Division of application No. 08/877,361, Jun. 16, 1997
[60] Provisional application No. 60/019,816, Jun. 17, 1996.

[51] Int. Cl.[7] ..................................................... C12P 19/34
[52] U.S. Cl. ................... 435/91.2; 435/91.5; 435/285.1; 435/287.2; 435/287.3
[58] Field of Search .................................... 435/91.1, 91.2, 435/91.5, 283.1, 285.1, 287.1, 287.2, 287.3; 937/77, 78, 88

[56] References Cited

U.S. PATENT DOCUMENTS

| | | | |
|---|---|---|---|
| 5,176,203 | 1/1993 | Larzul | 165/61 |
| 5,227,554 | 7/1993 | Chou | 585/303 |
| 5,270,183 | 12/1993 | Corbett et al. | 435/91.2 |
| 5,333,675 | 8/1994 | Mullis et al. | 435/6 |
| 5,415,839 | 5/1995 | Zaun et al. | 422/64 |
| 5,455,175 | 10/1995 | Wittwer et al. | 435/286.1 |
| 5,720,923 | 2/1998 | Haff et al. | 422/68.1 |
| 5,736,314 | 4/1998 | Hayes et al. | 435/4 |

*Primary Examiner*—David A. Redding
*Attorney, Agent, or Firm*—Charles K. Sholtz; Jeffery D. Frazier; LeeAnn Gorthey

[57] ABSTRACT

A thermocycling apparatus comprising a plurality of capillaries for moving DNA-containing samples between two or more discrete zones maintained at selected elevated temperatures.

6 Claims, 9 Drawing Sheets

THERMOCYCLING APPARATUS AND METHOD

This application is a division of application Ser. No. 08/877,361, filed Jun. 16, 1997 now allowed, which claims the benefit of priority of U.S. provisional application Ser. No. 60/019,816, filed Jun. 17, 1996 now abandoned, which are both incorporated herein by reference in their entirety.

FIELD OF THE INVENTION

The present invention relates to DNA thermocyclers, and in particular, to thermocyclers adapted for rapid temperature transitions with small fluid samples.

REFERENCES

Ausubel, F. M., et al., *Current Protocols in Molecular Biology* (John Wiley and Sons, Inc., Media, Pa.).

Corbett, et al., U.S. Pat. No. 5,270,183, issued February 1991.

Mullis, K. B., U.S. Pat. No. 4,683,202, issued Jul. 28, 1987.

Mullis, K. B., et al., U.S. Pat. No. 4,683,195, issued Jul. 28, 1987.

BACKGROUND OF THE INVENTION

Most currently-available thermocyclers are so-called "block thermocyclers". Such block thermocyclers have contributed much to the success of polymerase chain reaction (PCR; Mullis, Mullis, et al.) by allowing users a simple, convenient, and repeatable method for temperature cycling reactions. They allow very large volume reactions for preparative work, though this often requires re-optimization of the cycling parameters since temperature control is usually done on the block temperature and not the sample temperature. Due to the large sample size, block thermocyclers are relatively slow, with even the best machines (e.g., Perkin-Elmer 9600) capable of a maximal throughput of less than 1500 reactions per day. Further, block thermocyclers are typically among the most expensive in terms of per-sample reagent costs is (the Perkin-Elmer 9600 costs about $4.00 per sample).

Corbett, et al., describe a continuous serial-flow thermal cycler having a single long capillary tube wound around heating elements maintained at different temperatures. Different samples are serially passed through the same tube. The invention suffers from the disadvantages of potential sample contamination by residue left from a previous bolus, and inability to independently vary the dwell time or temperature for different samples.

Accordingly, a need exists for a rapid, efficient thermocycler. The present invention provides such a thermocycler—an apparatus capable of rapid amplification of small volume DNA samples, with minimal potential for cross-over contamination and capacity for independent regulation of the cycling parameters for each sample, at a per-sample reagent cost of less than $0.20.

SUMMARY OF THE INVENTION

The present invention includes, in one aspect, an apparatus for thermally cycling a DNA sample. The apparatus includes (i) a support and (ii) a heating unit assembly mounted on the support. The heating assembly has first and second heating elements defining first and second heating chambers, respectively, which are adapted to receive and contact a capillary tube. The capillary tube, which during operation of the apparatus contains the sample, extends through the two heating chambers. The apparatus further includes (iii) a means for maintaining the temperatures of the first and second chambers of the heating unit assembly at selected first and second elevated (i.e., above ambient) temperatures, and (iv) a means for moving the sample in the tube successively between the two chambers. The temperatures are typically selected such that one elevated temperature is effective to denature the DNA sample and the other elevated temperature is one at which DNA annealing and primer-directed DNA polymerization can occur.

In one general embodiment, the sample is moved in a reciprocating motion within the tubes by, for example, a mechanism which includes an integrated circuit (IC) motion controller (such as the Motorola 68HC711 microcontroller) and a movement unit, such as a direct current (DC) motor with a threaded rod, and a syringe body with a plunger. Other examples of movement units include a gated pressure/vacuum supply, a cascaded solenoid system, an electrostatic or piezoelectric diaphragm displacement, and "bimetallic" junction beam displacement (bending moment). In a syringe/plunger system, the moving means can include, for example, a syringe body, a plunger, and means for moving the plunger in a reciprocating motion within the syringe body (such as a DC motor connected to a threaded shaft). In certain embodiments, the moving means also includes a sample position feedback system.

The invention further includes embodiments wherein the apparatus is used with the sample disposed at a fixed region within the capillary tube, and the moving means includes means for moving the tube reciprocally between first and second positions effective to place the region within the first and second chambers of the capillary assembly, respectively.

In another embodiment, (i) each heating unit assembly further contains a third heating element defining a third heating chamber, (ii) the temperature maintenance means is effective to maintain the temperature of the third heating chamber at a selected third elevated temperature, and (iii) the sample moving means includes means for moving the samples in the tubes between the three chambers of each capillary assembly. In one preferred embodiment, the first elevated temperature is effective to denature the DNA sample, the second elevated temperature is one at which DNA annealing can occur, and the third elevated temperature is one at which primer-directed DNA polymerization can occur.

In a related embodiment, (i) each heating unit assembly further contains a cooling element defining a cooling chamber, (ii) the temperature maintenance means is effective to maintain the temperature of the cooling chamber at a selected below-ambient temperature, and (iii) the sample moving means includes means for moving the samples in the tubes between the two heating chambers and the cooling chamber of each capillary assembly.

The sample volume in each sample capillary of the above-described apparatus is preferably between about 0.5 and 5 µl, and the capillary tubes preferably have an interior face that is hydrophobic.

A general embodiment useful for thermally cycling a plurality of DNA samples comprises a plurality of heating unit assemblies (e.g., 8 or 12) mounted on a single support (e.g., at 9 mm interval for use with a 96-well plate). The sample moving means in such an apparatus may be designed to move the samples in all capillaries in a concerted manner, or to move them independently of one another. Further, the temperatures of the heating chambers of each heating unit assembly may be maintained independently of temperatures of the heating chambers of other heating unit assemblies. The heating unit assemblies, sample moving means and temperature maintenance means in such an apparatus may all be mounted on a single support, such as a module board. Such a module board may be used, for example, in an instrument capable of receiving a plurality of such module boards, to provide a planar array of DNA thermocyclers with a spacing corresponding to the wells of a 96-well plate. The boards adapted for use with such an instrument may be modified such that they contain only the mechanical and heating elements, with the instrument itself housing the majority of the electronic components. Further such boards may be condensed into a plastic "block" more suitable for repeated insertion and removal of capillaries. The spacing of the sample capillaries in such a block preferably corresponds to the spacing of wells in a 96-well plate.

In yet another general embodiment, the temperatures of the heating chambers of each heating unit assembly are maintained independently of the temperatures of the heating chambers of other heating unit assemblies. The temperature maintenance means in such an embodiment may include an integrated circuit (IC) temperature controller (such as the Motorola 68HC711), IC heater drivers and a temperature feedback system. Each capillary assembly preferably has an independent heater driver and temperature sensor. Examples of suitable temperature sensors include thermocouples, resistance temperature devices (RTD's), Proportional To Absolute Temperature (PTAT) circuits, and thermistors. The temperature feedback system preferably includes independent thermistor temperature sensors for each capillary assembly and an analog-to-digital (A/D) convertor.

In another aspect, the present invention includes a thermocycling apparatus for thermally cycling DNA samples containing primer and DNA polymerase reagents required for primer-directed amplification of the DNA. The apparatus includes (i) a capillary assembly, which includes (a) first and second heating elements, defining first and second heating chambers, respectively, (b) a capillary tube extending through the two heating chambers, and (c) a means for introducing one such DNA sample into the capillary tube; (ii) means for maintaining the temperatures of the first and second chambers of the capillary assembly at selected first and second elevated temperatures, wherein one elevated temperature is effective to denature the DNA sample and the other elevated temperature is one at which DNA annealing and primer-directed DNA polymerization can occur; and (iii) means for moving the samples in the tubes successively between the two chambers of each capillary assembly. In a preferred embodiment, the apparatus includes plurality of such capillary assemblies.

In one general embodiment, the sample moving means of the apparatus is effective to move the sample in a reciprocating motion within the tubes. Examples of such moving means include a syringe/plunger system (driven by, e.g., a small DC motor or a linear stepper motor), a gated pressure/ vacuum supply, a cascaded solenoid system, an electrostatic or piezoelectric diaphragm displacement, and "bimetallic" junction beam displacement (bending moment). In a syringe/plunger system, the moving means can include, for example, a syringe body, a plunger, and means for moving the plunger in a reciprocating motion within the syringe body (such as a DC motor connected to a threaded shaft).

In another general embodiment, the sample moving means is effective to move the samples in all capillary is assemblies in a concerted manner.

In an alternative general embodiment, the moving means is effective to move the samples independently of one another. Such a moving means may include, for example, an integrated circuit (IC) motion microcontroller (such as the Motorola 68HC711), movement units and a sample position feedback system. Each capillary assembly in such an apparatus has an independent movement unit and optionally, a sample position sensor, such as an optical sensor. The movement unit may include, for example, an IC motor driver, a direct current (DC) motor with a threaded rod, and a syringe body with a plunger.

Also included in the invention is an embodiment wherein the samples are adapted to be disposed at fixed regions within the tubes, and the moving means includes means for moving the tubes reciprocally between first and second positions effective to place the regions within the first and second chambers of each capillary assembly, respectively.

In yet another general embodiment, the temperatures of the heating chambers of each capillary assembly are maintained independently of the temperatures of the heating chambers of other capillary s assemblies. The temperature maintenance means in such an embodiment may include an integrated circuit (IC) temperature controller (such as the Motorola 68HC711), IC heater drivers and a temperature feedback system. Each capillary assembly preferably has an independent heater driver and temperature sensor. Examples of suitable temperature sensors include thermocouples, resistance temperature devices (RTD's), Proportional To Absolute Temperature (PTAT) circuits, and thermistors. The temperature feedback system preferably includes independent thermistor temperature sensors for each capillary assembly and an analog-to-digital (A/D) convertor.

In another general embodiment, the apparatus contains 8 or 12 linearly-disposed capillary assemblies spaced at 9 mm intervals. In a related embodiment, the capillary assemblies, sample moving means and temperature maintenance means are mounted on a single module board, which can be used in an instrument containing a plurality of such module boards. The boards adapted for use with such an instrument may be modified such that they contain only the mechanical and heating elements, with the instrument itself housing the majority of the electronic components. Further such boards may be condensed into a plastic "block" more suitable for repeated insertion and removal of capillaries. The spacing of the sample capillaries in such a block preferably corresponds to the spacing of wells in a 96-well plate.

In a preferred embodiment, (i) each capillary assembly further contains a third heating element defining a third heating chamber, (ii) the temperature maintenance means is effective to maintain the temperature of the third heating chamber at a selected third elevated temperature, wherein the first elevated temperature is effective to denature the DNA sample, the second elevated temperature is one at which DNA annealing can occur, and the third elevated temperature is one at which primer-directed DNA polymerization can occur, and (iii) the sample moving means includes means for moving the samples in the tubes between the three chambers of each capillary assembly.

In a related embodiment, (i) each capillary assembly further contains a cooling element defining a cooling chamber, (ii) the temperature maintenance means is effective to maintain the temperature of the cooling chamber at a selected below-ambient temperature, and (iii) the sample moving means includes means for moving the samples in the tubes between the two heating chambers and the cooling chamber of each capillary assembly.

The sample volume in each sample capillary of the above-described apparatus is preferably between about 0.5 and 5 μl, and the capillary tubes preferably have an interior face that is hydrophobic.

Also included in the invention is a related apparatus for thermally cycling a DNA sample. The apparatus includes (i) a support; (ii) a heating unit assembly mounted on the support, the assembly having first and second heating elements defining first and second heating chambers, respectively, the chambers being adapted to receive and contact a capillary tube, containing the sample, extending through the two heating chambers; (iii) a temperature control system having a temperature controller electrically connected to a power delivery system and a temperature feedback system, the power delivery system being connected via leads to the heating elements, and the feedback system including temperature sensors in the heating elements, wherein the controller regulates power delivered to each heating element via the power delivery system based on signals from the feedback system, in order to maintain the temperatures of the first and second chambers of the heating unit assembly at selected first and second elevated temperatures; and (iv) a sample position control unit adapted to connect and form a seal with a first end of the capillary tube, and being effective to alter pressure at the first end, the altering of pressure being effective to move a DNA sample in the tube successively between the two chambers.

The invention further includes a method of amplifying target DNA using an apparatus such as described above. The method includes the steps of loading a sample containing target DNA, dNTPs, thermostable DNA polymerase (e.g., Taq polymerase) and primers into an apparatus as described above, and cycling the sample between at least two elevated temperatures effective to result in primer-specific amplification of the target.

These and other objects and features of the invention will become more fully apparent when the following detailed description is read in conjunction with the accompanying drawings.

DETAILED DESCRIPTION OF THE INVENTION

I. Thermal Cycling Apparatus

A. Overview

Figure 1A:
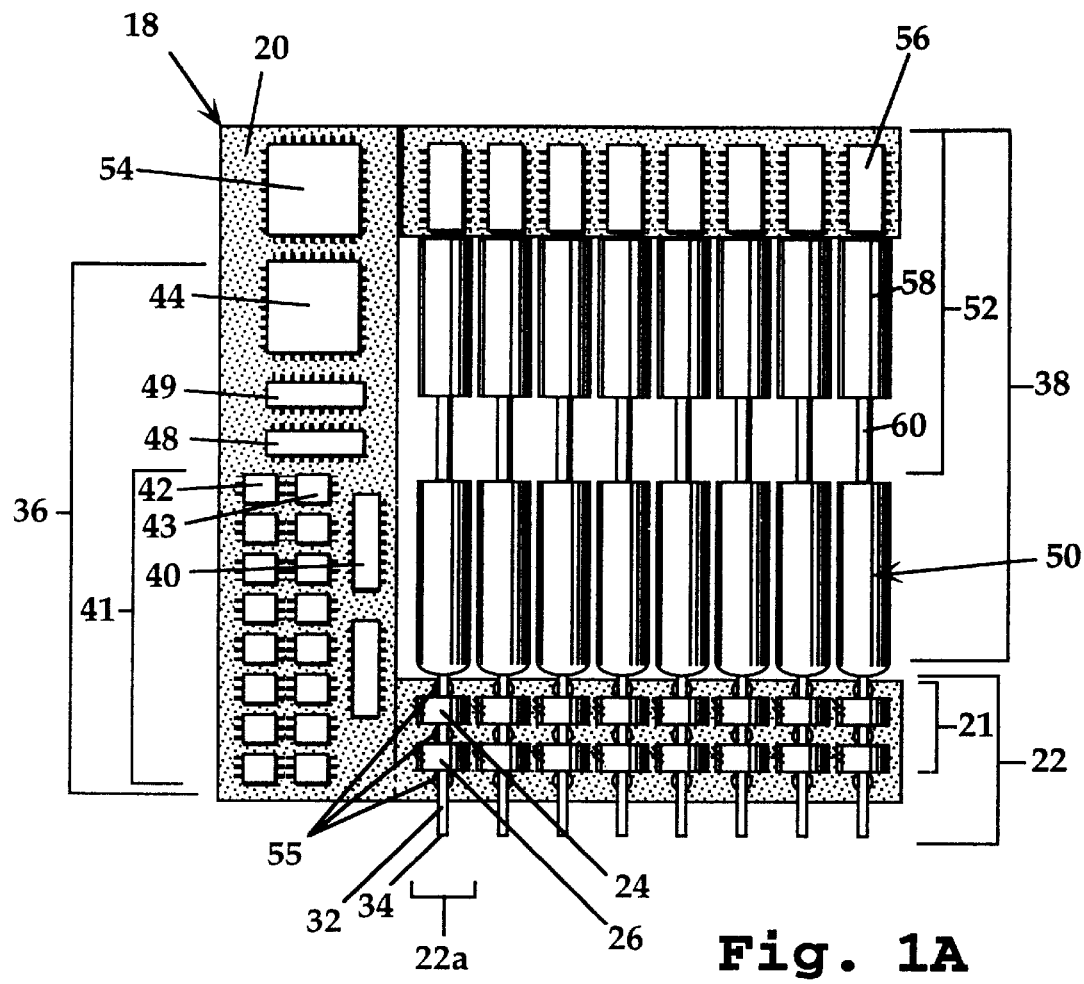
FIG. 1A is a plan view of a thermocycling apparatus constructed according to the present invention.
Figure 1B:
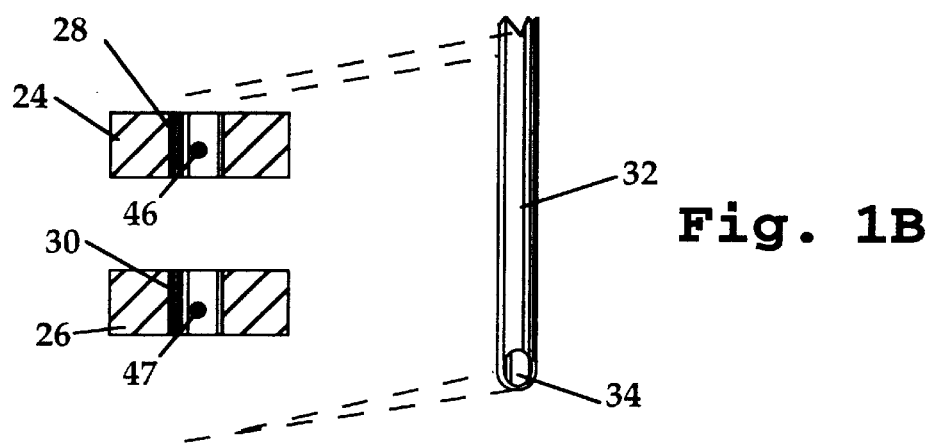
FIG. 1B is a sectional/exploded view of an capillary assembly constructed according to the present invention.

FIG. 1A illustrates, in plan view, an apparatus or device 18 constructed according to the present invention. The apparatus is mounted on a support, preferably a single module board 20, and includes one or more (e.g., 8) heating unit assemblies 21. Each heating unit assembly contains at least two heating elements, such as first heating element 24 and second heating element 26, defining two heating chambers, such as first heating chamber 28 and second heating chamber 30, shown in the exploded view of FIG. 1B. The heating chambers are adapted to receive a capillary tube 32 extending through the heating chambers 28 and 30. As is described in greater detail below, the DNA sample to be amplified is introduced into the capillary tube through a port or opening, such as opening 34.

In one embodiment, the capillary tube is included as part of the apparatus. In such cases, the apparatus contains one or more capillary assemblies 22, such as assembly 22a. Each capillary assembly contains, in addition to the at least two heating elements and heating chambers, a capillary tube 32.

Referring again to FIG. 1A, the apparatus further includes a temperature maintenance system 36 for maintaining the temperatures of the first and second chambers of such a capillary assembly at selected first and second elevated temperatures, as well as a sample position control unit for moving the samples in the tubes successively between the two heating chambers of each assembly. In the embodiment illustrated in FIG. 1A, the sample position control units include movement units 38.

The temperature maintenance system in the embodiment shown in FIG. 1A is effective to maintain the temperatures of the heating chambers of each heating unit or capillary assembly independently of the temperatures of the heating chambers of other assemblies. This may be accomplished as shown, by utilizing independently-controlled heating elements, such as elements 24 and 26. Power is delivered to the elements by a power delivery system 41, which in the pictured embodiment includes power transistors (e.g., one of the eight transistors in integrated circuit (IC) chip 40) and IC heater drivers, such as heater drivers 42 and 43. The heater drivers control the power transistors and are in turn controlled by an IC temperature controller 44. The controller is typically a microprocessor, such as a Motorola 68HC711, that regulates the power to each IC heater driver based on the desired temperature of the heating chamber supplied by that driver and information obtained from the temperature feedback system from that chamber.

The temperature feedback system typically includes temperature sensors, a multiplexer, and an analog-to-digital (A/D) converter. In embodiments such as shown in FIG. 1A, where the temperature of each heating chamber is independently controlled, each heating chamber has a temperature sensor, such as thermistors 46 and 47 in FIG. 1B. The thermistors in this embodiment are used as one leg in a voltage divider (described more fully below), and the output of this circuit is routed via a multiplexer, such as multiplexer 48 in FIG. 1A, to an A/D converter 49. The A/D converter digitizes the output of the thermistors and relays the information to the temperature controller 44.

In other embodiments, such as those described below with reference to FIG. 6, the temperature of the corresponding regions of two or more heating unit or capillary assemblies may be regulated by a single heating element, which defines corresponding heating chambers in each heating unit or capillary assembly.

The apparatus is adapted to be used with, or includes, a capillary for holding the DNA sample during the amplification process. Both ends of the capillary are initially open. The distal end (the "bottom" end, at opening 34 of FIG. 1B) typically remains open. After the capillary is positioned in the apparatus and the DNA sample is introduced (these steps may be done in either order although the given sequence is more typical), the end attached to the sample position control unit ("top" end) may either remain open or may be sealed off by the sample position control unit, depending on the method by which the sample is moved relative to the heating chambers. In embodiments where the motion of the sample between different heating chambers is accomplished by moving the entire capillary, with the samples disposed at fixed regions within the tubes (described more fully below), the state of the top end is not particularly important, although as a practical matter it will typically be sealed off by the sample position control unit.

In embodiments where the sample is moved inside a fixed capillary, however, the top end needs to be sealed off from the ambient by the sample position control unit, so that pressure changes in the capillary between the sample and the sample position control unit can result in motion of the sample relative to the capillary. In addition, the interior surface of capillary tube in such applications is preferably a non-wetting hydrophobic surface. This allows the sample to be moved from a first region in the tube to a second region without leaving a portion of the sample in the first region. The capillaries may either be purchased with an interior hydrophobic coating, or they may be coated with a hydrophobic material (e.g., silanized) prior to use.

The sample moving means in the embodiment of FIG. 1A is designed to move the sample in a reciprocating motion within the tubes, by changing the fluid pressure at the sealed end of the capillary. Fluid pressure in this context includes air pressure, in cases where air is the "fluid" between the sample plug and the structure responsible for the pressure change, as well as the pressure exerted by a mechanical element, e.g., a syringe plunger, directly on the sample. It also, of course, refers to the pressure of an inert fluid such as mineral oil that may be used to communicate pressure changes from the structure responsible for the pressure change to the DNA sample. Examples of structures or mechanisms which may be used in designing or making such a sample moving means include a syringe/plunger system in combination with a linear stepper motor or DC motor, a gated pressure/vacuum supply, a cascaded solenoid system, electrostatic or piezoelectric diaphragm displacement, and "bimetallic" junction beam displacement (bending moment).

The sample position control unit includes control elements that regulate or control the timing, rate and extent of sample movement, and movement unit(s), that generate and/or transmit the physical force (e.g., air pressure change) causing the sample to move. The control elements typically include an integrated circuit (IC) motion controller 54 such as a Motorola 68HC711microprocessor, and a sample position feedback system, which may include a sample position sensors, such as optical sensors 55. In embodiments such as illustrated in FIG. 1A, the samples may be moved independently of one another since the assemblies all have independent corresponding movement units 38 and independent sample position sensors.

The movement units 38 illustrated in FIG. 1A each include a syringe body and plunger, shown together at 50, and plunger moving means 52 for moving the plunger in a reciprocating motion within the syringe body. The plunger moving means 52 includes an IC motor driver, such as driver 56, and a direct current (DC) motor 58 with a motion translation means 60.

Other embodiments may employ structures which move the samples in all capillaries in concert rather than independently. Still other embodiments may employ designs where the moving means does not move the fluid within the capillary, but rather, moves the entire capillary within the heating chambers described above. In such embodiments, the samples are adapted to be disposed at fixed regions within the tubes. In operation, the capillary tubes are moved reciprocally between first and second positions effective to place the fixed regions within the first and second chambers of each capillary assembly, respectively.

B. Sample Position Control Units In embodiments where the (fluid) sample is moved between different temperature regions inside a stationary capillary, the force which moves the sample is typically a change in the pressure of the fluid (typically air) column above the sample. Such a pressure change may be effected by a number of different mechanisms, including a syringe/plunger system in combination with a linear stepper motor or DC motor, a gated pressure/vacuum supply, a cascaded solenoid system, electrostatic or piezoelectric diaphragm displacement, and "bimetallic" junction beam displacement (bending moment). Such mechanisms, which are effective to move the sample between different temperature regions, together with any electronics that may control or regulate their operation, are examples of sample position control units, or moving means.

An exemplary way of moving a fluid sample inside the capillary is with positive-displacement motion. Positive displacement motion is routinely-used in conventional syringes and pipettors. The underlying principle is a piston moved by linear motion in a region sealed by the sample on one side and a sliding seal around the piston on the other. As described below, the linear motion may be created by turning a helical shaft (constrained for no axial motion) in a matching nut (constrained for no rotary motion).

In a preferred embodiment, the individual capillary assemblies match the spacing of a standard is laboratory 8*12 96-well plate having sample wells approximately 9 mm apart. Such an apparatus typically contains either 8 or 12 capillary assemblies next to one another, spaced at approximately 9 mm, corresponding to one of the sides of the plate. The mechanical portion of the movement unit (i.e., the movement unit without the IC chip motor driver) should therefore fit into a 9 mm by 9 mm cross-sectional area.

A sample position control unit having the above-described characteristics may be fashioned using a 6 volt, 8 mm DC motor with matching 64:1 gearheads, available from Micro Mo Electronics Inc. (Clearwater, Fla.) as part number 0816P006S+08/1, 64:1. This motor operates at a no-load speed of 16000 RPM and stalls at $0.39 \times 10^{-3}$ Nm. The gearhead efficiency is 70% with a maximum output torque of 60 mNm continuous, 120 mNm peak. Assuming 100% efficiency in the screw/nut connection, this gives a maximum linear speed of 1.9 mm/s and maximum force of 11 N (though the gearhead bearings are rated at 3 N of maximum axial force).

Figure 2:
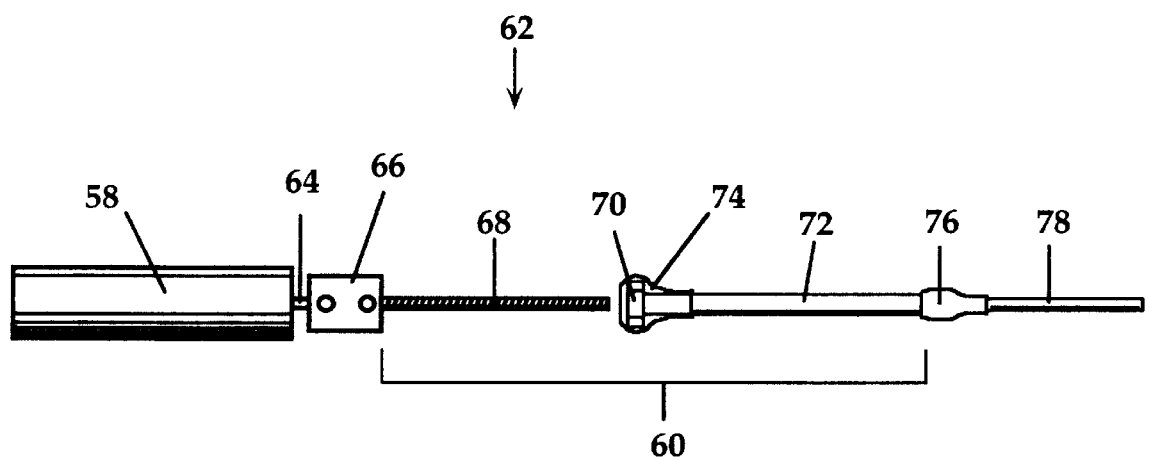
FIG. 2 is a plan view of the mechanical portion of one element of sample moving means.

An exemplary mechanical portion 62 of an individual movement unit with dimensions suitable for use with a 96-well plate is shown in FIG. 2. The output shaft 64 of the DC motor 58 gearhead is rigidly connected via a Delrin shaft coupling 66 to a #2 threaded rod 68 with a pitch of 56 threads per inch (TPI). The threaded rod is fashioned to threadably engage a #2–56 mating nut 70, which is constrained from rotation but allowed to slide in a machined groove. The nut 70 is attached to a hollow stainless steel tube 72 with heat shrink tubing 74. The tube 72 provides space for the threaded rod to fill as the nut moves toward the motor. The other end of the tube is attached with heat shrink tubing 76 to a precision ground stainless steel shaft 78, which forms the "plunger".

FIG. 3 shows a detailed cross-section view of a portion of an apparatus of the present invention containing eight assemblies 22 and eight corresponding movement units. A backing spring 80 provides upward force on the nut when the piston assembly, consisting of the nut 70, tube 72 and shaft 78, is extended away from the motor 58.

Figures 3A, 3B:
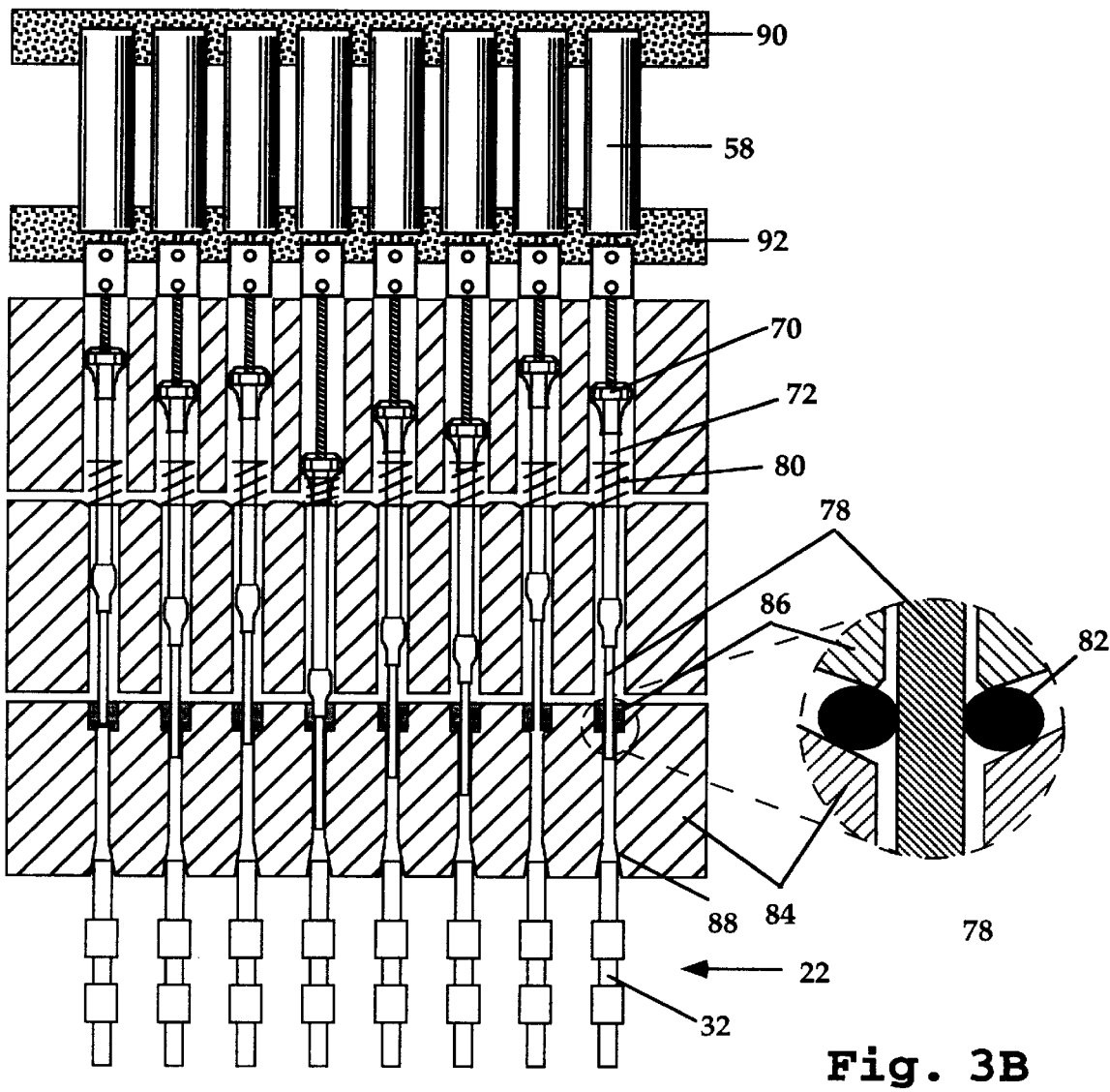
FIG. 3A is a sectional view of the sample-moving portion and capillary assemblies of the apparatus in FIG. 1A.
FIG. 3B is a detailed view of a seal in FIG. 3A.

As shown in FIG. 3B, an "o-ring" 82 is used to form a sliding seal around the precision shaft 78. The o-ring is retained on top of the syringe body 84 by a hollowed-out set screw 86 (e.g., a ¼–20 set screw). The syringe body is preferably made of clear plastic to allow visual inspection of the sealing surfaces and the position of the piston end. A capillary tube 32 is seated into a tapered hole 88 in syringe body 84. The motor 58 is shown mounted in upper 90 and lower 92 motormounts.

The embodiment described with reference to FIGS. 3A and 3B has less than 1% variation in time of motion for each channel after an initial wear in time of 24 hours of continuous operation.

C. Temperature Control Hardware

The temperature control hardware exemplified in the apparatus illustrated in FIG. 1A includes 2 basic elements—temperature sensor and heating element. Thermistors are used as the temperature sensors for the apparatus shown in FIG. 1A because they offer high sensitivity, can be read directly by an analog to digital converter, and are available in small sizes (down to 0.005" if necessary). The thermistors, obtained from Thermometrics (Edison, N.J.; Part Number BR16-K-A-103), were supplied with nominal (25° C.) is resistance of 10 kohms, +/−20% and were therefore calibrated before use. Thermistors with lower variability may of course also be used.

Further, other types of temperature sensors may be employed, including thermocouples. While thermocouples are considerably cheaper, they are less sensitive, are susceptible to noise when routed in areas of large thermal transients, and require additional expensive circuitry to amplify and optionally linearize their signals before being digitized. They could be used effectively, however, if for example they were connected to copper circuit board traces at uniform temperature junctions very near the point of measure. Other possibilities for temperature measurement include resistance temperature devices (RTD's) and Proportional To Absolute Temperature (PTAT) circuits. By using an RTD, the sensor/heater pair can be replaced with one device to provide resistive heating and temperature sensing. PTAT circuits are designed to require no calibration but are at present not commercially available in the correct size range.

Figure 4A:
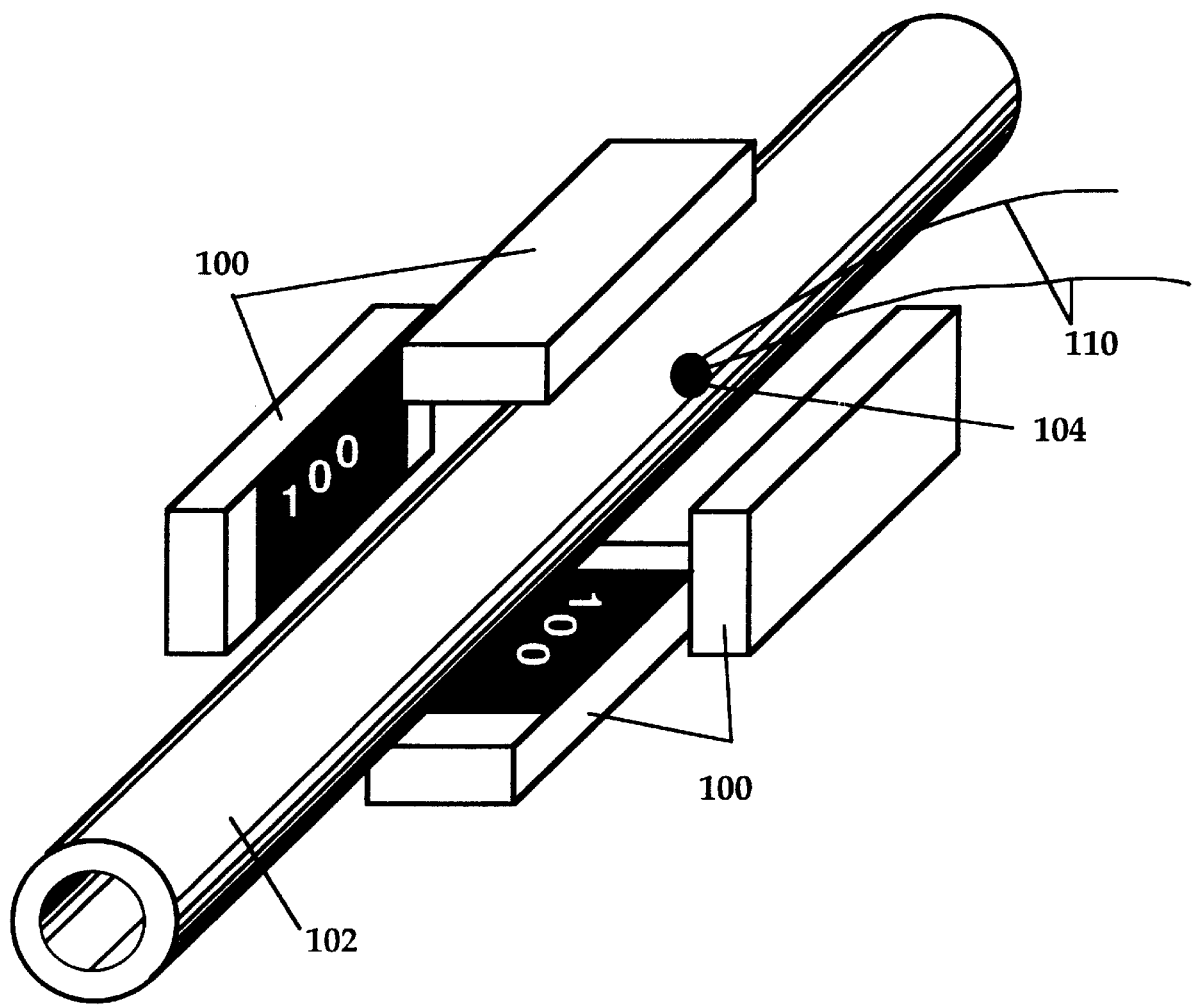
FIG. 4A is an exploded view of a step in the assembly of a heating/sensor element shown in FIG. 1A.

The heating elements used in the apparatus shown in FIG. 1A are assembled from commercially available, surface mount thick film resistors (Mouser Electronics, Gilroy, Calif.; Part Number 263-100). With reference to FIG. 4A, four such resistors 100 are epoxied with thermally conductive epoxy (Omega Engineering, Stamford, Conn.; Part Number OB-101) around a section of Teflon tubing 102 having the same outer diameter as the capillary sample tube.

Figure 4B:
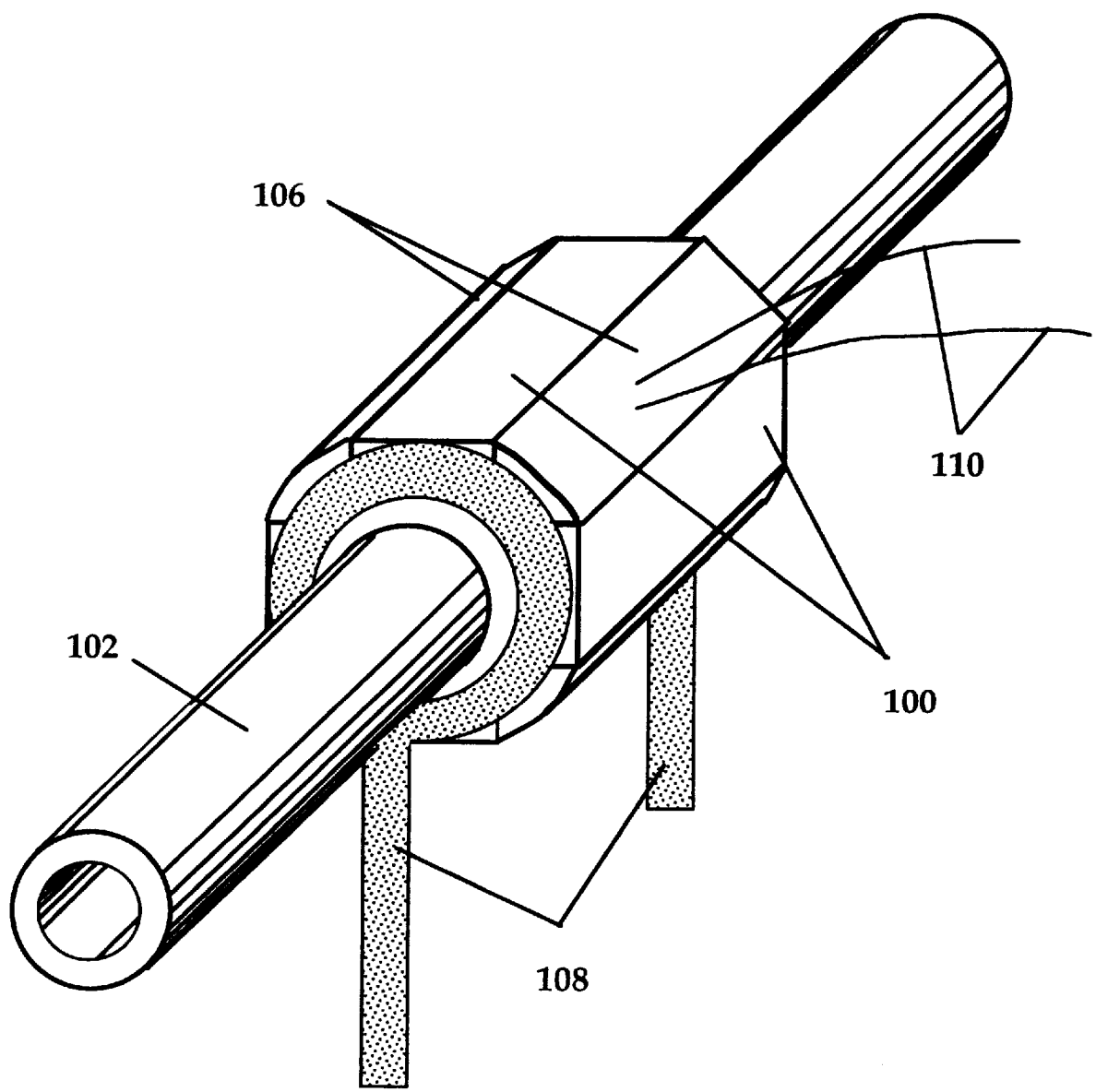
FIG. 4B is a perspective view of a partially-completed heating/sensor element shown in FIG. 1A.

Just before placing the last heater, the temperature sensor 104 is pushed into the epoxy. The finished structure is shown in FIG. 4B, with epoxy portions shown at 106. The epoxy is allowed to set overnight and then the four resistors 100 are soldered to 36-gage copper wire 108 so that they are electrically connected in parallel. The leads from the thermistor are indicated at 110. The Teflon tube is withdrawn, yielding the final heater/sensor assembly.

In the final stage of manufacture, the heater/sensor assembly is inserted into a mounting structure which can be fastened onto a module board (such as a circuit board) holding the apparatus. This structure serves to constrain motion of the heater/sensor along the tube axis and rotationally around the tube axis while being free enough to center itself on the axis of the tube as the capillary sample tube is inserted. Insertion of the capillary may be facilitated by a tapered opening region effective to guide the sample capillary into the snug confines of the heating chamber.

The heater/sensor assembly encased in such a mounting structure should preferably contact as little support material (i.e., circuit or module board in the case of an assembly as in FIG. 1A) as possible to provide better thermal isolation among the various heaters and between heater and the printed circuit board. Like several of the drive system components, it may be conveniently cast from polyurethane with up to 5\% w/v hollow glass microspheres (Tap Plastics, Mountain View, Calif.). This dramatically decreases the mounting structure's density and thermal conductivity, again providing better thermal isolation to each heater. In a preferred embodiment, the heater/sensor assembly is attached to the printed circuit board only by the soldered connections of the heaters and temperature sensors; due to the number of these connections and small size of the overall assembly, such an attachment is sturdy enough for repeated use.

Directed radiation may also be employed as a means to apply heat to different regions of the capillary tube, although the power required (5 W per 8 channels) is relatively high.

Alternatively, heat may be supplied by pumping water or other fluid that is maintained at a selected temperature in an external reservoir, such as a water bath, through thermally-conductive jackets forming the heating elements.

D. Other Embodiments

Figure 5:
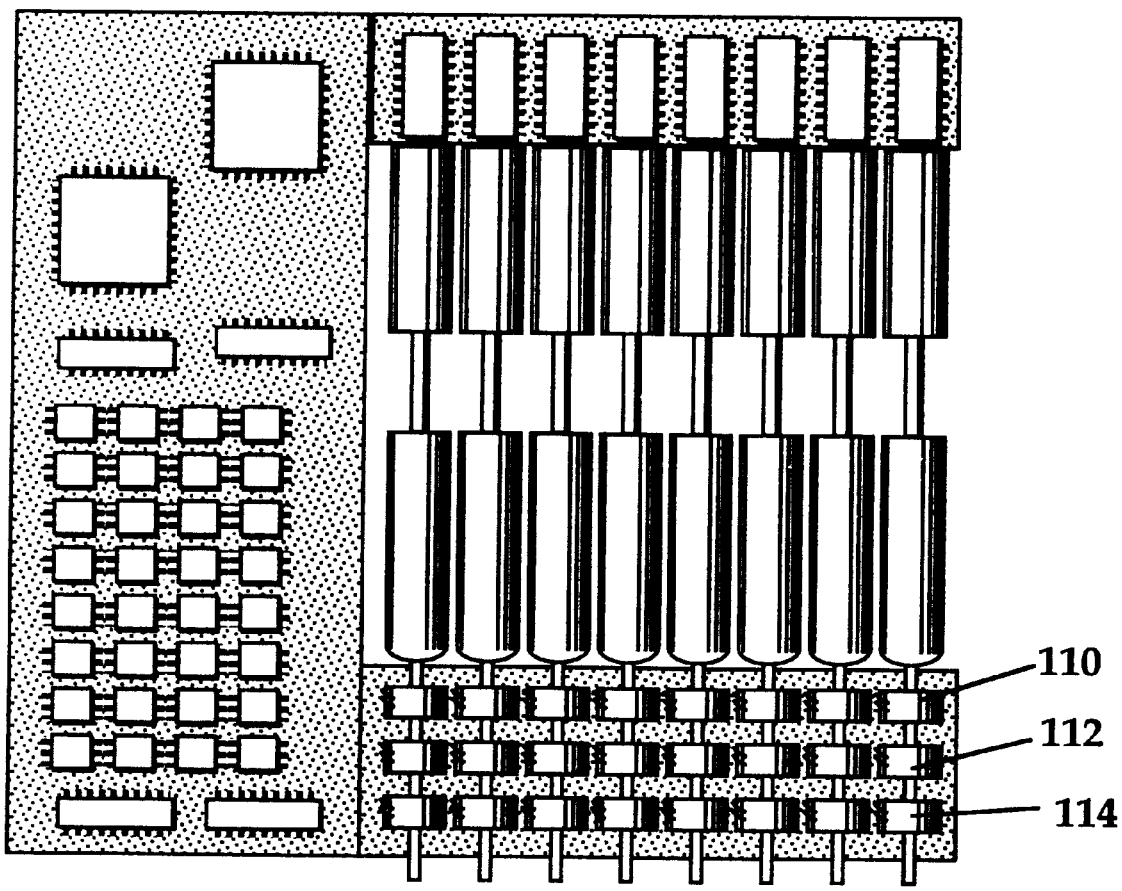
FIG. 5 is a plan view of a preferred embodiment of an apparatus of the present invention.

FIG. 5 shows a preferred embodiment of the present invention. It is analogous in all respects to the apparatus described with reference to FIGS. 1A, 1B, 2, 3A, 3B, 4A and 4B, except that each capillary assembly contains 3 separate heating chambers, formed by 3 separate heating elements, 110, 112 and 114, and preferably containing 3 separate temperature sensors—one for each heating element. The third chamber of each capillary assembly provides a third temperature zone through which the DNA sample may cycled, and enables, e.g., 3-temperature polymerase chain reaction (PCR; Mullis, Mullis, et al.) employing a denaturing temperature, an annealing temperature and an extension temperature. Other relevant portions of the apparatus, such as the structures and controls that are part of the sample moving means, are of course adapted so that the sample may be moved between the three zones or regions.

An apparatus of the present invention may also be constructed to contain, in addition to the two or more heating chambers as described above, a cooling chamber. The cooling chamber may be disposed on the apparatus in an analogous manner to the heating chambers. For example, with reference to FIG. 5, elements 110 and 112 could be heating elements forming heating chambers and element 114 could be a cooling element forming a cooling chamber. A cooling chamber is useful, e.g., for keeping the sample contents refrigerated (e.g., at 4° C.) either before initiation of or after completion of a run. The cooling chamber is constructed in a manner analogous to the heating chamber (e.g., as described with reference to FIGS. 4A and 4B), but with substitution of cooling elements for heating elements. An exemplary cooling element suitable for this purpose is a Peltier element, which can pump heat from one side of the element to the other. The remaining elements of the apparatus, particularly those used for control or maintenance of the cooling chamber temperature at a desired value, are of course selected by the practitioner of the invention using known approaches such they will function properly with such a cooling chamber.

In another general embodiment, an apparatus of the present invention may be designed more economically by combining one or more of the individual sample moving and/or temperature maintenance means into single structures, such that the samples in two or more sample capillaries, and/or the temperatures at corresponding zones of two or more capillaries, are moved or adjusted together by a single structure or element. An example of such an embodiment is shown in FIG. 6. Here, a single movement unit 120 is used to move the DNA samples in eight individual capillary assemblies. The capacity of such a movement unit must of course be increased relative to that required for a movement unit connected to a single capillary assembly, typically by a factor approximately equal to the number of capillary assemblies 122 serviced by such a movement unit. The air pressure changes can be communicated to the individual capillaries by, for example, a manifold, such as manifold 124, which includes tapered air-tight adapters 126 for retaining the sample capillaries.

Figure 6:
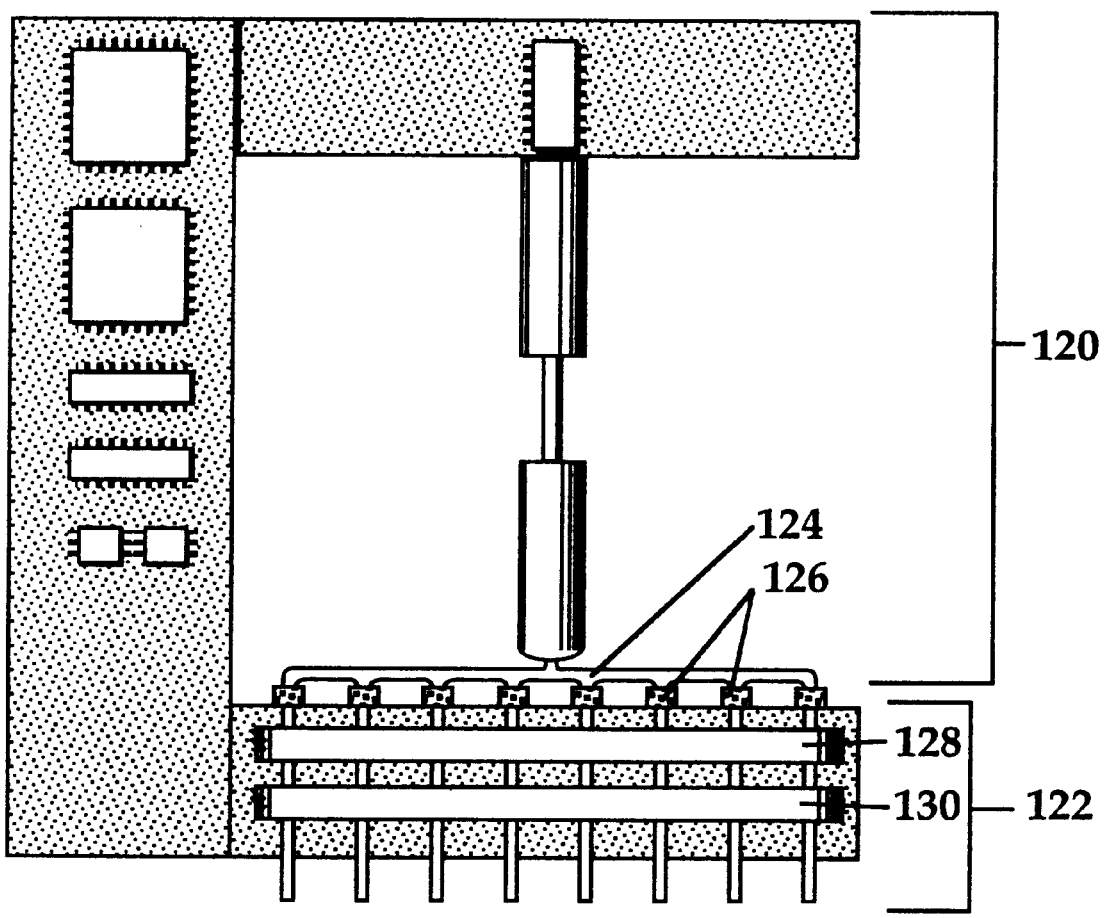
FIG. 6 is a plan view of an alternate embodiment of an apparatus of the present invention.

The apparatus shown in FIG. 6 also contains only two heating elements, 128 and 130. Each element defines the eight heating chambers corresponding to the eight capillaries at one of the elevated temperature zones. In other words, the eight capillary assemblies "share" a single "first heating element" 128 and a single "second heating element" 130. Accordingly, each heating element is designed such that the heating chambers defined by the element are at substantially the same temperature.

It will be appreciated that alternate embodiments of the present invention can contain variations of the above. For example, an apparatus may have a single movement unit for every two or four capillary assemblies. Similarly, an apparatus may have a single heating element for every two or four heating chambers in two or four capillary assemblies.

As described in reference to FIG. 1A, and illustrated in FIGS. 1A, 5 and 6, a thermocycling apparatus of the present invention is preferably mounted on a module board support, such as a circuit board. This feature allows the apparatus to be mounted in an instrument adapted to contain a plurality of such module boards, e.g., via standard printed circuit board connector slots, such as bus slots. The instrument can be used to coordinate the action of the individual module boards to carry out, for example, PCR amplification on 96 samples simultaneously.

Figure 7:
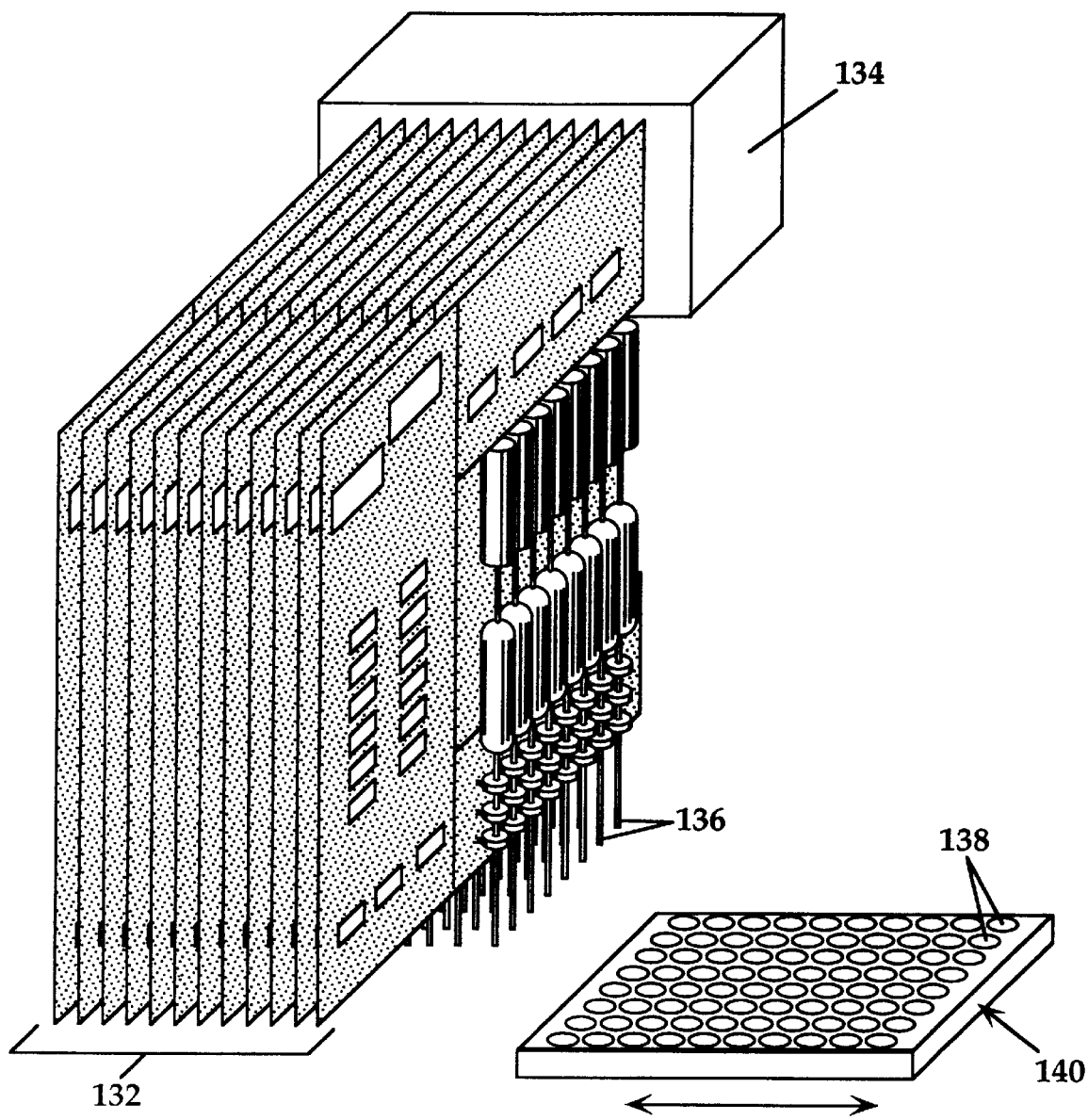
FIG. 7 is a perspective plan view of 12 thermocycling apparatuses of the present invention positioned in an instrument at a spacing corresponding to the wells of a 96-well laboratory plate.

The boards in such an instrument are preferably mounted at a spacing corresponding to the spacing of wells in a selected laboratory container, preferably a 96-well plate. FIG. 7 shows the arrangement of 12 module boards in such an instrument 134. The capillary assemblies on each board, as well as the boards themselves, are spaced such that the inlet ends of the capillaries 136 are spaced at the same spacing as the wells, such as wells 138, of a 96-well plate 140.

II. Operation of Thermal Cycling Apparatus

The operation of an apparatus constructed according to the present invention may be conveniently performed using the electronic components and software algorithms described below. The specific components and parameters employed in these sections are provided as examples of specific working embodiments, and are not meant to limit the scope of the invention.

1. Motion Control Electronics

Motion control electronics are the electronic components associated with the sample movement means of the present invention. They contain three basic elements: sample movement or motion controller, motor driver, and sample position feedback system. In embodiments where the drive system is extremely stable, the feedback system might not be necessary. A feedback system is desirable in embodiments utilizing changes in air pressure to move the sample, since such air is typically exposed to varying temperatures, causing it to change volume.

As mentioned above and described in more detail below, a microprocessor such as the Motorola MC68HC711 microcontroller is an exemplary sample movement controller. It interfaces with the driver electronics by providing one on/off bit and one direction bit to each of the IC motor drivers, such as Harris Semiconductor HIP4020IB motor drivers. The interface to the feedback system is through analog multiplexers which allow the microprocessor to select which optical sensor is electrically connected to it's analog inputs.

The Motorola MC68HC711 microprocessor was used in part because it can digitize these analog inputs directly without another stage of amplification or discretization. Of the 38 microprocessor input/output (I/O) pins available, 8 are dedicated to reading the analog signals from the optical sensors, 16 to motion control (1 on/off bit, 1 direction bit per motor), 4 to driving the analog multiplexers, and 2 to serial communications. The remaining ports may be used to communicate with other devices or the external world via displays and pushbutton inputs.

Cycle parameters were downloaded through a standard RS-232 protocol which the microprocessor comes equipped to handle. In the example described, it was necessary to shift the standard RS-232 voltage levels to CMOS compatible voltages; the Harris Semiconductor HIN232 accomplished this while operating on a single 5V supply.

Harris Semiconductor HIP4020IB motor drivers were used because they are completely self-contained full H-bridge motor drivers capable of providing 100 mA bidirectionally to the motors, which draw 44 mA nominally at their rated voltage (6V). Speed control was provided by using a separate power supply and ground for the motor voltage, although the motor can be operated effectively using the same motor voltage as the electronics drive voltage (5.8V). If desired, the current limit error output from the motor drivers may be monitored by the controller during the run. Alternatively or in addition, the output may be used to drive LED's to indicate error to the user.

Sample position feedback was accomplished through infrared optical interrupters (Optek H22B1) mounted on either side of the sample tubing, with their signals digitized by A/D converters integrated in the microcontroller. When the sample obstructs the path of the light, it reduces the amount of scatter on the interior tube wall, thus increasing the transmitted light and reducing the voltage at the photodarlington's collector. The voltages at these 24 collectors were multiplexed through analog multiplexers (Harris Semiconductor DG409) such that each of the eight analog inputs of the microcontroller could be switched to one of the three sensors on each sample tube (i.e., one analog input served the three sensors on one sample tube). A 0.5 volt drop in collector voltage was common when a sample arrived at an interrupter. The A/D converters on the microcontroller were 8-bit converters with high and low references tied to supply voltage (5.8V) and supply ground, so that the signal was typically well above noise.

Under certain conditions, ambient 60 Hz radiation may be sufficient to confuse sensor readings; this can be corrected by selecting optical components whose packages are opaque in all directions but the direction of sensing. Although no capacitive elements were employed in the above-described embodiment due to space constraints on the board, such capacitive elements may be included, e.g., upstream of the signal multiplexers, in other embodiments to improve response time or reduce noise in the sensing circuits. Filtering and failsafe systems exist in software in the event of a sensor failure.

2. Motion Control Software

Software for the motion control system or sample movement means was typically stored onboard the motion controller (e.g., onboard the Motorola 68HC711 microcontroller in EPROM memory). The Motorola 68HC711 is advantageous from a software implementation standpoint as well as providing ample I/O, because it allows a number of powerful control and error correction schemes to be implemented in software, thus decreasing hardware development and debugging time. The software was written in assembly language for the microcontroller to maximize system performance.

All events were timed using the internal Real Time Interrupt (RTI) system which was configured to increment a 16-bit counter once every 27.3 mS. This set the minimum event length as well as the maximum latency to check each channel's state and suffer no timing error. The software has 4 sequential functional modes; data entry, sample loading, sample cycling, and sample unloading.

Data entry permits the user to download new cycle parameters or use existing ones and then begin a run. The data to be downloaded typically includes times at each of the three positions for each sample (in clock ticks, 27.3 mS per tick) and number of cycles in each tube as well as "tuning" parameters. The tuning parameters are fractional amounts of the movement time which must be added during motion to ensure that the sample moves from the optical sensor, where sample detection is made, into the heated regions a few millimeters away. Note that since the times are downloaded as 16-bit unsigned integers, the longest hold time available is 23.7 mS*$2^{16}$=25.8 hours.

Lastly, the length of time required to unload the samples is downloaded. These parameters are echoed back to the user. They may then be stored in EEPROM for this run and subsequent runs. Alternatively, the user may chose parameters already in EEPROM or they may chose to enter the data again. Some parameters can be programmed to have special meaning; for example, 0 cycles specified for one channel leaves that channel completely unmoved for the entire run.

Prior to loading samples, the apparatus was initialized. As described above with reference to FIG. 3A, a backing spring 80 provides upward force on the nut when the piston assembly, consisting of the nut 70, tube 72 and shaft 78, is extended away from the motor 58. The apparatus was initialized with respect to sample position (e.g., when it is first turned on for an experiment) by spinning the motor to push the piston assembly off the end of the threaded rod. The presence of the backing spring allowed the nut to engage the threaded rod when the direction of the motor was reversed ("inward motion") to draw sample in.

To load samples, inward motion was started and the lowest optical sensor was monitored. When fluid reached this sensor in a particular tube, motion stopped for that channel. Once all eight sensors had been tripped, motion was started for a short, fixed length of time which was downloaded with the cycle parameters. This pulled the sample from just below the optical sensor into the region of the first heater.

After all samples were loaded, the software entered a polled mode of operation. A small program loop checked each channel in turn for any of these events:

1. Is this channel finished cycling? If so, begin unloading process.
2. Is the channel motor not moving? If not, should it start?
3. Is the channel motor moving? If so, should it stop now?
4. Have all channels been unloaded? If so, quit this loop.

Since unloading is part of the polled loop, nothing is left to be done after the loop ceases. A final printout of run data is provided and the apparatus resets itself.

During this polled mode of operation, the user may modify the contents of any RAM location, query the current status of the apparatus, or reset the microcontroller. The apparatus can be queried for current run conditions or for the current program. Data returned for current run conditions includes number of cycles done, current time count, and current sample position.

For current program, the apparatus returns the number of cycles programmed, time at each heater position, and fraction of motion required to reach the next heater after tripping an optical sensor. Motion between the optical sensors is monitored to check for sensor failures. After each motion, the time taken for that motion is stored in RAM. During the next cycle, when that motion is again repeated the optical sensor is only monitored after some fraction (1−1/T2) of the previous move time has elapsed. This prevents premature stops due to faulty sensing. Similarly, if the move has taken (1+1/T1) longer than the previous move, motion is immediately stopped and the movement time is set as that for the previous correct move.

3. Temperature Maintenance Electronics

The electronics for temperature maintenance or control typically include a temperature controller, power delivery system, and temperature feedback system. The Motorola 68HC711 is an exemplary temperature controller for many of the same reasons that it is an exemplary sample movement controller, and was therefore selected for use as the temperature controller with the working embodiments described herein. In the temperature maintenance system, however, additional resolution was desired for the temperature control so that reactions could be done as precisely as possible. Therefore, an analog-to-digital (A/D) converter separate from the one incorporated in the microcontroller was used for analog to digital conversion of the temperature sensor signal. Further, the temperature feedback system in the preferred embodiments is required and is not optional as it was with the sample moving means, since changes in ambient conditions can cause very large changes in temperatures in devices of this size.

Of the 38 I/O pins available on the microcontroller, 12 were used to read the parallel-output 12 bit analog to digital converters, 3 to select between the three A/D converters, 4 to multiplex the analog temperature sensor lines to the three A/D converters, 2 to communicate with the PWM (heater control) circuits, 6 to select between the PWM circuits, and 2 to communicate with the user via RS-232. The microcontroller thus provided ample basic I/O for the exemplified embodiments as well as room for additional features, such as direct drive of an output device (e.g. an LCD panel) or pushbutton operation. Note that the same HIN232 (dual)

RS-232 level shifting chip was used to interface both this microcontroller and the motor driver to the standard RS-232 levels.

The heater drive was pulse width modulated (PWM). In this mode of operation, the duty cycle of a constant frequency (e.g., 17 kHz) square wave was modulated to control the power to the heating elements. To provide a selected amount of power to a heater or heating element, the microcontroller computed a control value, ranging from 0 to 100% of the maximum power output. The microprocessor then selected the appropriate PWM circuit (Harris Semiconductor CDP68HC68W1) and transmitted the control value to that circuit via a high speed serial communication link. The PWM circuit then modulated its output square wave to match the transmitted duty cycle. This square wave output (5 V TTL level) controlled one of eight darlington power transistor (part ULN2803A), each of which is capable of switching over 1 W of power. When the transistors were switched on (by a high level from the PWM circuit), they connected one side of the resistive heater with ground, generating heat where required.

The positive side of the heater is an independent supply and may be connected to any voltage (e.g., up to 24 V). In the exemplified embodiments, this supply was tied to the rest of the board supply at 5.8 V to allow for battery operation. Noise filtering may be included to reduce the 17 kHz driving signal, e.g., by placing a 470 $\mu$F capacitor between the supply and ground near the darlington transistors.

It will be noted that in the PWM mechanism, the output voltage, and not output power, is proportional to duty cycle. This is relevant with respect to control schemes discussed in the software section below.

The temperature sensing circuitry was a voltage divider with one leg being the thermistor and the other being a precision thin film metal resistor with a relatively low temperature coefficient. The resistance R was selected to provide near-linearity of the resultant voltage with temperature in the range of 50 to 100° C. The output voltage ($V_o$) of the divider network is given by:

$$V_0 = \frac{V_+}{1 + (R_T(T)/R)}$$

is where $V_+$ is the supply voltage, $R_T(T)$ is the thermistor resistance (which varies with temperature), and R is the lower leg resistor. This equation is recast by defining two new quantities:

$$s = \frac{R_{T0}}{R}$$

$$r_T = \frac{R_T}{R_{T0}}$$

where s is a constant, the ratio of the thermistor resistance at a reference temperature (25° C. in this case) to the lower leg resistor R. $r_T$ now captures all the temperature dependence of the thermistor, normalized to the thermistor resistance at the reference temperature. $r_T$ is a function of the materials used in the thermistor and is provided in tabular form from the manufacturer. Substituting these quantities into equation 1 and normalizing with respect to supply voltage, one obtains $$F(T) = \frac{V_0}{V_+} = \frac{1}{1 + sr_T(T)}$$

By analyzing a plot of F(T), it will be appreciated that s=8 provides a fairly linear F(T) over 50 to 100° C. R can now be found directly from equation 2, R=$R_{T0}$/S=10 kohms /8=1250 ohms. R=1270 ohms was chosen as it is the nearest higher commercially available resistor.

To reduce costs, thermistors with up to +/−20 variation in their nominal $R_{T0}$ values may be used. However, such variability affects both the linearity of the voltage divider output with temperature as well as the absolute readings taken from the A/D system. For these reasons, an apparatus using such variable thermistors is preferably calibrated after final assembly to directly associate A/D readings with actual sample temperatures.

There eight voltage divider outputs of each row of sensors were connected to one Harris Semiconductor DG408 analog multiplexer. The inputs to these two (in the case of two-temperature cyclers) or three (in the case of three-temperature cyclers) multiplexers are gated to the output under the control of the microcontroller. The multiplexer outputs were digitized by Harris Semiconductor HI5812 12 bit analog to digital (A/D) converters. The distance between multiplexers and A/D converters did increase the amount of noise on the sensor lines. However, since the time constant of the heater/sensor assembly was on the order of a few seconds, and the microprocessor read temperatures and updated heater outputs twice per second, this random noise did not significantly affect temperature control.

4. Temperature Maintenance Software

There are many similarities and considerable code reuse between the motion control software described above and the temperature maintenance or control software. In the illustrated embodiments, the temperature control software has two phases: the user inputs data for the run or selects pre-loaded data, and then the software enters a continuously polled mode of operation to monitor temperature and modify heater power. The user may modify any area of RAM, query the apparatus's status and latest readings, or reset the microcontroller at any time during this polled mode. In this way, subtle changes to temperatures can be made during a run. This control methodology allows completely independent settings on each of the heater/sensors.

A brief discussion of a suitable control algorithm is provided to illustrate how the temperature can be controlled. This control algorithm is a simple proportional-integral scheme, commonly used in heater control where the thermal inertia of the system is large relative to the power input available. The amount of power to be applied to the system is given by:

$$Y = K_p(T_{ref} - T_{meas}) + \frac{1}{K_i} \int_0^\tau (T_{ref} - T_{meas}(\eta)) d\eta$$

where $T_{ref}$ and $T_{meas}$ are target and measured temperatures, respectively, represented as A/D counts. This control scheme theoretically allows for zero steady-state error at equilibrium ($T_{ref}=T_{meas}$), as the integral term will set the heater power necessary to maintain a constant temperature. The integral term is discretized using a second order central difference scheme (i.e., trapezoidal rule integration):

$$\int_0^t (T_{ref} - T_{meas})(\eta) d\eta \approx I_j = \frac{\Delta\eta}{2}[(T_{ref} - T_{meas,j}) - (T_{ref} - T_{meas,j-1})] + 1$$

The j–1 quantities are updated and stored in RAM each time a new control value is calculated. The integral term ($I_j$–1) is stored as a 16-bit unsigned value with a sign bit stored separately in 3 reserved bytes. The software prevents "integrator wind-up" by not adding more to the integral term once control has been saturated (full power is applied).

Since the control value (Y) computed above is power (the physical driving force which will change the temperature) but the control electronics only allow specification of voltage, a correction must be made to the control value. In the resistive heating used here, the actual power applied to the heater is given by $P=v^2/R$ where v is the applied voltage and R is the (assumed constant) heater resistance. Thus the correct control value to present to the heater control circuitry is actually square root of Y. Note that the maximum control value valid for the heater control circuitry is 255; thus a 16-bit unsigned Y value will not overflow the maximum control.

The data down loaded by the user is a set of 24 temperature setpoints in A/D counts ($T_{ref}$), one proportional constant ($K_p$), and one integral constant ($K_i$). As with the motion controller, that data are then echoed back through the serial port. The user can either accept that response and program it into EEPROM, disregard that input and run with values currently stored in EEPROM, or enter the data again.

Once begun, the polled mode of operation indexes through each of the heater elements, checking temperature, computing a new heater control value, and writing out that value if it has changed since the last update By only updating heater output when a new value is needed, the PWM signal is interrupted as little as possible since the PWM circuits must be deactivated to receive new control conditions. As mentioned above, the user may freely view or modify any region of RAM while this polled mode is in operation. If new control values were inserted into memory over the old ones, the system would drive to meet these new values. The system may also be reset or queried at any time during the polled operating mode.

III. Applications

An exemplary application of an apparatus constructed according to the present invention is thermal cycling of target DNA-containing samples having primer and DNA polymerase reagents required for primer-directed amplification of the DNA. Reagents typically employed in such amplification reactions include reaction buffer containing $MgCl_2$, dNTPs, a primer set and a thermally-stable DNA polymerase (e.g., Taq polymerase). Reaction conditions for various amplifications are well known in the art (see, e.g., Mullis, Mullis, et al., Ausubel, et al.).

Samples containing the selected reagents, such as DNA target, primers, dNTPs and polymerase, are introduced into the capillaries by placing the open ends of the capillaries into vessels containing the mixture to be cycled, and applying negative pressure at the back (upper) ends of the capillaries. In an exemplary embodiment, the negative pressure is applied by withdrawal of a plunger in a syringe body, as illustrated in FIG. 3A. The plunger may be withdrawn by rotation of the threaded rod 68 in a direction effective to move the nut 70 toward the motor 58.

The volume of the samples depends on the design of the device—devices employing relatively large-diameter capillaries and/or devices employing heating elements that extend over a substantial portion of the sample-containing capillary can accommodate a larger sample than devices employing small-diameter capillaries and/or devices employing "narrow" heating elements that extend over a relatively small portion of the sample-containing capillary. Devices designed for small-diameter capillaries have several advantages. For example, sample evaporation is minimized, cycle speed is increased and the size, power consumption and cost of components is reduced, since the total heat capacity of the "plug" of sample is smaller. The embodiments described herein are designed for sample volumes in the range of between about 0.5 and 10 µl per capillary, preferably in the range of between about 0.5 and 5 µl per capillary.

After loading of samples, the apparatus can begin the thermal cycling process using, for example, a protocol programmed as described in the above software sections. In a typical PCR reaction, the sample is denatured at a "first" relatively high temperature (e.g., 96° C.) for several minutes, and then cycled between either two or three temperatures for a selected (e.g., 30) cycles. In a two temperature protocol, the second temperature is one at which the primers can selectively and specifically anneal to the target DNA and primer-directed DNA polymerization can occur (e.g., 60° C.). In a three temperature protocol, the second temperature is one at which the primers can specifically and selectively anneal to the template DNA (e.g., 55° C.) and the third temperature is one at which primer-directed polymerization can occur efficiently (e.g., 72° C.).

Figure 8:
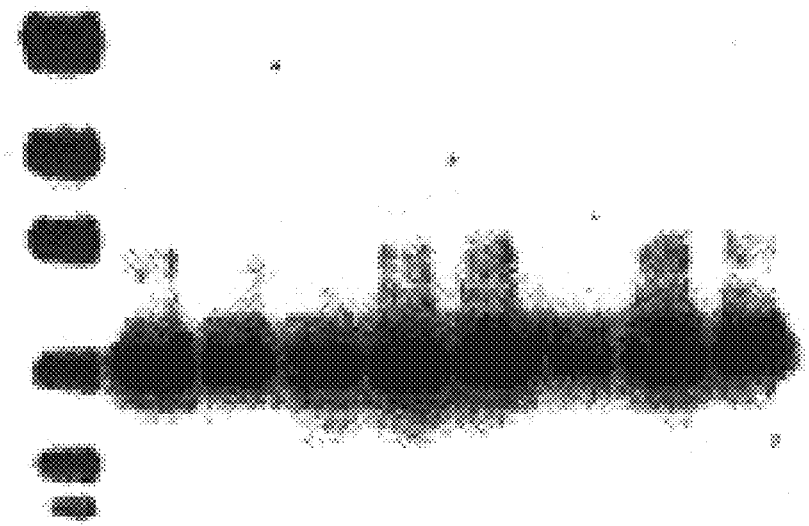
FIG. 8 is a negative computer-generated image of an ethidium bromide stained agarose gel containing polymerase chain reaction amplification products generated using an apparatus constructed according to the present invention.

An apparatus such as illustrated in FIG. 5, containing eight capillary assemblies, was used to PCR amplify target M13 mp template containing a yeast DNA insert using M13(–21) and M13(–48) primers and Taq polymerase for 32 cycles at 44 sec per cycle. Amplification products resolved on an agarose gel and visualized using ethidium bromide are shown in FIG. 8. Lane markers are in the first (left) lane. The next eight lanes contain the reaction products from the eight sample capillaries of the apparatus.

Other applications of the thermocycling apparatus of the present invention include cycle sequencing and restriction digests. Cycle sequencing is a variation on PCR, where the reaction is typically carried out using labeled primers.

Thermocycling devices or apparatuses of the present invention provide a number of advantages over existing thermal cyclers. Among these are the following: they have a very rapid cycle time (as short as 15–30 sec per cycle); they use small sample volumes (typically 0.5–5 µl, preferably 0.5–3 µl); each sample can be individually programmed for different cycle temperatures and durations; and low power consumption.

IV. Production Considerations

Many of the more complex hardware components can be fabricated by creating a silicone RTV mold of the original part and casting subsequent copies with a 2-part polyurethane (Tap Plastics) using known techniques. Parts which are preferably machined are typically specified with large tolerances and require no surface finish. Electronics and programming software are commercially available from a variety of vendors.

While the invention has been described with reference to specific methods and embodiments, it is appreciated that various modifications and changes may be made without departing from the invention.

It is claimed:

1. A method of amplifying target nucleic acid, comprising the steps of:

introducing a sample containing target nucleic acid, nucleotides, enzyme and primers into a capillary tube mounted on a support; said capillary tube having a sample position control unit, including a syringe body and a plunger movable within the syringe body, disposed in communication therewith;

maintaining first and second regions of said tube at respective first and second temperatures;

altering the pressure within said tube by moving said plunger in a reciprocating motion within said syringe body, thereby moving the sample within said tube successively between said first and second regions in a reciprocating motion, such that the sample is cycled between at least two temperatures in a manner effective to result in primer-specific amplification of the target.

2. The method of claim 1, wherein (i) said target nucleic acid is DNA; (ii) said nucleotides are dNTPs; and (iii) said enzyme is a DNA polymerase.

3. A method of amplifying target nucleic acids, comprising the steps of:

introducing a plurality of samples, each containing target nucleic acid, nucleotides, enzyme and primers, into respective capillary tubes mounted on a support;

maintaining first and second regions of each tube at respective first and second temperatures;

moving the samples within all of said tubes in a concerted manner between said first and second regions, thereby cycling the samples between at least two temperatures in a manner effective to result in primer-specific amplification of each target.

4. The method of claim 3, wherein (i) each target nucleic acid is DNA; (ii) said nucleotides are dNTPs; and (iii) each enzyme is a DNA polymerase.

5. A method of amplifying target nucleic acid, comprising the steps of:

introducing a sample containing target nucleic acid, nucleotides, enzyme and primers into a capillary tube mounted on a support;

operating a temperature control unit disposed in communication with a heating unit assembly, both mounted on said support, to maintain first and second regions of said tube at respective first and second temperatures;

operating a sample position control unit, mounted on said support, to move the sample within said tube between said first and second regions, thereby cycling the sample between at least two temperatures in a manner effective to result in primer-specific amplification of the target.

6. The method of claim 5, wherein (i) said target nucleic acid is DNA; (ii) said nucleotides are dNTPs; and (iii) said enzyme is a DNA polymerase.

* * * * *

UNITED STATES PATENT AND TRADEMARK OFFICE
CERTIFICATE OF CORRECTION

PATENT NO. : 6,132,996  
DATED : October 17, 2000  
INVENTOR(S) : Scott P. Hunicke-Smith Page 1 of 1

It is certified that error appears in the above-identified patent and that said Letters Patent is hereby corrected as shown below:

<u>Title page,</u>
Line 9, insert
-- This invention was made with Government support under Grant HG00205 awarded by the National Institute of Health. Accordingly, the U.S. Government may have certain rights in the invention. --

Signed and Sealed this

Twenty-third Day of April, 2002

Attest:

JAMES E. ROGAN
*Director of the United States Patent and Trademark Office*

*Attesting Officer*